United States Patent [19]

Bender et al.

[11] Patent Number: 4,777,250

[45] Date of Patent: Oct. 11, 1988

[54] CHYMOTRYPSIN MODEL

[75] Inventors: Myron L. Bender; Valerian T. D'Souza, both of Evanston, Ill.

[73] Assignee: Northwestern University, Evanston, Ill.

[21] Appl. No.: 876,278

[22] Filed: Jun. 19, 1986

[51] Int. Cl.$^4$ .................. C08B 30/18; C08B 37/16; C12N 9/16; C12N 9/76; B01J 37/36; B01J 31/00

[52] U.S. Cl. .................. 536/46; 435/196; 435/213; 502/7; 502/107; 536/103

[58] Field of Search ............ 435/140, 156, 213, 183, 435/196; 536/46, 103; 502/7, 167

[56] References Cited

PUBLICATIONS

D'Souza, V. T., Hanabusa, K., O'Leary, T., Gadwood, R. C. and Bender, M. L. (1985) Biochem Biophys Res Commun 129,727.
Breslow, et al., Bioorg, Chem., 12, 206–220 (1984).
Van Etten, R. L. et al., J. Am. Chem. Soc., 89, 3253–3262 (1967).
Mallick, et al., J. Am. Chem. Soc., 106, 7252–7254 (1984).
Breslow, et al., J. Am. Chem. Soc. 100, 3227–3229 (1978).
Breslow, et al., J. Am. Chem. Soc. 105, 1390–1391 (1983).
Angew, Chem. 78, 641 (1966).
Schonbaum, G. R. et al., J. Biol. Chem., 236, 2930–2935 (1961).

*Primary Examiner*—Thomas G. Wiseman
*Assistant Examiner*—Charles L. Patterson, Jr.
*Attorney, Agent, or Firm*—Tilton, Fallon, Lungmus & Chestnut

[57] ABSTRACT

Low molecular weight chymotrypsin analogs exhibiting the binding and catalytic groups of the real enzyme of the formula

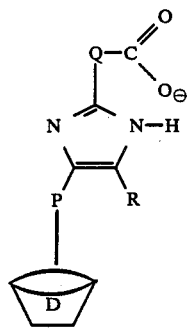

where D equals $\alpha$-, $\beta$- or $\gamma$-cyclodextrin; P is X or $(CH_2)_nX$, wherein n equals 0 to 2 and X equals S, NH, or 0; Q equals substituted phenyl with the carboxylate ion attached to the ortho position or equals $(CH_2)_n$, wherein n equals 0 to 3; and R equals hydrogen —$CH_3$ or —$C_2H_5$.

The enzyme models are useful as an analytical model mimicking the real enzyme, a stain remover, a laundry detergent additive, a food additive, and as a therapeutic agent for treating enzyme deficiencies.

17 Claims, 2 Drawing Sheets

CHYMOTRYPSIN MODEL

BACKGROUND OF THE INVENTION

Enzymes are proteins with biocatalytic activity which exhibit high specificity, i.e., their power to catalyze the reaction of only certain molecules, with large rate accelerations. Although they are large and complex molecules, their power to catalyze reactions can be attributed to only two phenomena, binding and catalysis. Binding not only contributes largely to the specificity of the reaction but by stereochemistry also brings the substrate into close proximity and in the correct orientation to the catalytic site, which is ultimately responsible for the large rate accelerations which operate intramolecularly. Indeed, there are other factors: the microscopic environment of the reaction site; the stabilization of the transition state by hydrogen bonding, etc., which contribute toward the enzymatic activity in different enzymes by varying degrees; but binding, particularly of the transition state, and catalysis are the two essential features of all enzymes.

Enzyme modeling is the science of scientifically mimicking the exact nature of the binding site in terms of shape, size and microscopic environment; as well as the catalytic site in terms of identity of groups, stereochemistry, interatomic distances of various groups and the mechanism of action of the enzyme. Such information about the enzymes can be obtained by amino acid sequencing, CPK modeling, X-ray crystallographic studies, inhibition studies and specificity studies of the enzyme. It is known, for example, that the binding site for chymotrypsin is hydrophobic in nature, 10–12 Å deep and 3.5 to 5.5 to 6.5 Å in cross section, which gives a snug fit to an aromatic ring, also hydrophobic in nature, which is 6 Å wide and 3.5 Å thick. The active site of chymotrypsin has been shown to contain only three amino acids, namely serine 195, histidine 57 and aspartate 102. The unique feature about these amino acids, however, is the functional groups which they carry. They are shown in Table I and consist of a hydroxyl group of serine 195, an imidazole group of histidine 57 and a carboxylate ion of aspartate 102.

TABLE I

The Chymotrypsin Active Site

| AMINO ACID | FUNCTIONALITY |
|---|---|
| 1. serine 195 | hydroxyl |
| 2. histidine 57 | imidazolyl |
| 3. aspartate 102 | carboxylate ion |

The well-known "proton transfer relay" system proposed for the mechanism of action of chymotrypsin consists of two proton transfers, one initiated by the carboxylate ion and the other initiated by the imidazole to increase the nucleophilicity of the hydroxyl oxygen atom of serine toward the carbonyl function of the amide or ester substrate bound in the hydrophobic pocket of the enzyme to give an acyl-enzyme intermediate. Deacylation occurs via the same two proton transfers increasing the nucleophilicity of the hydroxyl group of water, which attacks the carbonyl group ($C=O$) of the acyl-enzyme ester.

A model of chymotrypsin should essentially contain a hydrophobic pocket to act as a binding site attached to a hydroxyl group (OH), an imidazole group

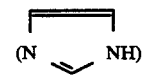

(N⤺NH)

and a carboxylate ion ($CO_2^-$) placed at the right distances and correct stereochemistry to participate in a "proton transfer relay" system.

Cramer has disclosed methods of modifying cyclodextrin by imidazole to produce a chymotrypsin model (Angew, Chem. 78, 641 (1966)), and Breslow et al. have disclosed methods of synthesizing models of ribonuclease, transaminase, and a thiazolium dependent enzyme based on cyclodextrin (Breslow, et al., J. Am. Chem. Soc. 100, 3227–3229 (1978); Breslow, et al., J. Am. Chem. Soc. 105, 1390–1391 (1983); and Breslow, et al., Bioorg. Chem., 12, 206–220 (1984)). In both Cramer's and Breslow's models, the catalytic groups are linked to C-6 of cyclodextrin, placing it on the primary edge of the molecule. It is placed in that location in distinction to the secondary (C-2, C-3) faces of the molecules. Apparently, the secondary side is more open and is the preferential locus of binding of large molecules for it is also the face on which the chirality of cyclodextrin is more apparent. The Cramer model is relatively unreactive.

SUMMARY OF THE INVENTION

The present invention provides a low molecular weight chymotrypsin analog having the same activity, binding and catalytic groups of the real enzyme. The enzyme model is more stable than the real enzyme because it contains no amino acids.

DETAILED DESCRIPTION

Figure 1:
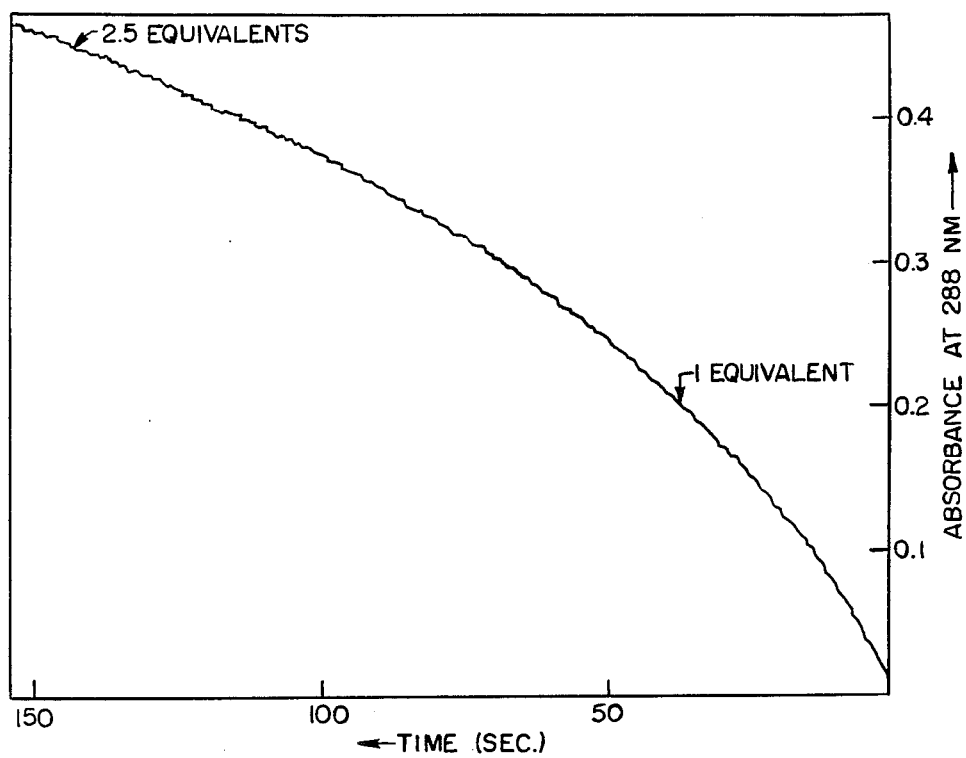
FIG. 1 graphically represents the catalysis of product formation versus time with a concentration ratio of substrate to enzyme of 2.5.

Chymotrypsin is a member of a family of enzymes known as serine proteases, so named because they have an unusually reactive serine residue at their active sites. It is a large molecule with a molecular weight of 24,800 and 245 amino acids. The molecular weight of the chymotrypsin model of this invention is only 1,365.

The chymotrypsin model of this invention may have many uses, all of which are identical to the real enzyme, such as a laundry detergent additive, stain remover, therapeutic agent, etc. However, the chymotrypsin model of this invention would be nonallergenic and more reactive at higher alkaline (pH) and temperature conditions, making it preferable to the natural enzyme. The model is more stable at high alkalinity and temperature since it contains no amino acids. In food, it could be utilized for its meat tenderizing abilities, and in medical therapy, it could be utilized to correct or prevent enzyme deficiencies.

The present invention provides a chymotrypsin model or analog represented by formula I:

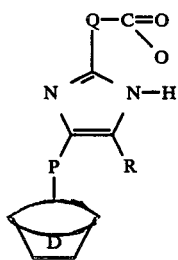

wherein D is α-, β- or γ-cyclodextrin; P is X or $(CH_2)_nX$, wherein n is 0 to 2 and X is S, NH, or O; Q is substituted phenyl with the carboxylate ion attached to the ortho position, or $(CH_2)_n$, where n is 0 to 3; and R is hydrogen, —$CH_3$ or —$C_2H_5$. Typically, when the hydrogen of the imidazole group bonds with the carboxylate ion, it will form a 6, 7 or 8-centered ring.

The three functional groups are indicated at Nos. (1), (2) and (3) of the preferred embodiment formula II:

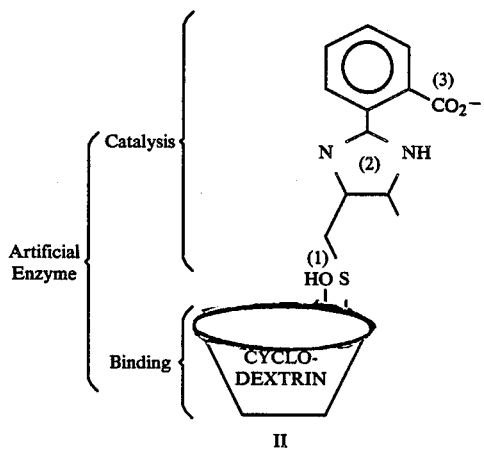

The foregoing preferred compound is identified as $3^A$-S-[[2-(2-carboxyphenyl)-5-methyl-1H-imidazol-4-yl]methyl]-$3^A$-thio-β-cyclodextrin. Other preferred compounds are $3^A$-S-[[2-(2-carboxyphenyl)-5-methyl-1H-imidazol-4-yl]methyl]-$3^A$-thio-γ-cyclodextrin and $3^A$-S-[[2-(2-carboxyphenyl)-5-methyl-1H-imidazol-4-yl]methyl]-$3^A$-thio-α-cyclodextrin.

In addition to the low molecular weight of the enzyme model, it has other differences to distinguish it from the real chumotrypsin. The model is nonproteinic and therefore does not denature easily. The model has a pH maximum of beyond 10 whereas the pH maximum for the real enzyme is 7.9. However, the model enzyme has the two essential features of the real enzyme, namely the binding and catalysis groups which render it functionality identical to the real enzyme.

Binding of the substrate to the enzyme is an essential feature of all enzymatic reactions. Usually binding of the substrate to the active site of the enzyme involves non-covalent forces such as hydrophobic and Van Der Walls, although covalent enzyme substrate bonds are formed during subsequent reaction. The binding site of chymotrypsin is essentially hydrophobic in nature and is capable of having maximum interaction with an aromatic ring to orient the oxygen atom of serine 195 for a nucleophilic attack on the carbonyl carbon atom of the ester or amide substrate. The ideal molecule on which to base a model of chymotrypsin should have a cavity of: (a) a maximum hydrophobic interaction with a substrate to form complexes; (b) should fit the aromatic ring of the substrate; and (c) the carbonyl carbon of the bound substrate should be oriented toward the oxygen atom of serine (acylation) or water (deacylation) for nucleopholic attack.

Cyclodextrins consisting of six, seven, or eight α-1,4-linked D-glycopyranoses are suitable for binding. Cyclodextrins have doughnut shapes with secondary hydroxyl groups at the C-2 and C-3 atoms of glucose units arranged in one open end and primary hydroxyl groups at the C-6 atoms of the glucose unit located at the other open end. Thus, the whole molecule is hydrophilic. However, the interior of the cavity, consisting of a ring of C-H groups, a ring of glycosidic oxygen atoms and another ring of C-H groups, is hydrophobic in nature, similar to the binding site of chymotrypsin. The inner diameters of the cavities are approximately 4.5 Å in α-cyclodextrin, 7.0 Å in β-cyclodextrin, and 8.5 Å in γ-cyclodextrin. Cyclodextrins bind with dissociation constants for aromatics ranging from $10^{-2}$ to $10^{-3}$M depending upon the substituents on the ring which are within the range of some enzymatic dissociation constants.

The stereochemistry of binding by cyclodextrin can be shown by the binding of m-t-butylphenyl acetate and p-t-butylphenyl acetate (Van Etten, R. L. et al., J. Am. Chem. Soc., 89, 3253–3262, 3253 (1967)). The binding of meta-substituted phenyl acetate to cyclodextrin orients the carbonyl carbon atom of the ester substrate toward the oxygen atom of the secondary hydroxyl groups of the cyclodextrin (nucleophilic attack). The complexes of para-substituted phenyl esters have the carbonyl carbon atom far from the secondary hydroxyl groups. This arrangement establishes support for the use of cyclodextrins in the chymotrypsin model.

An important feature of the mechanism of action of chymotrypsin is that there are two distinct phases: (a) the acyl transfer from the substrate to the hydroxyl group of the enzyme (acylation) to give the acyl-enzyme; and (b) the deacylation of the acyl-enzyme (ester) by water. A common feature in both reactions is that the negative charge from the carboxylate ion is transferred to the oxygen atom of the carbonyl function and, concurrently, the proton is transferred from the hydroxyl group of the serine in the first reaction and of water in the second reaction via the imidazole group to the carboxylate ion during the formation of the tetrahedral intermediate. This mechanism is known as the "charge relay" or more likely "proton transfer relay".

The system which mimics the catalytic site of chymotrypsin was constructed and investigated initially by placing an imidazole and a cinnamoyl ester function in endo-endo, 2-, 5-positions of a norbornane molecule. The imidazole group is shown to act as a general base catalyst and not a nucleophilic catalyst. The rate of deacylation is increased in the presence of benzoate ion, the third component of the active site. Additionally, the rate further increases in the presence of dioxane which is used to simulate the apolar nature of the active site of chymotrypsin. The ratio of the rates in the presence of 0.5M benzoate ion to that in the absence of benzoate ion results in a 2500 fold acceleration at a dioxane mole fraction of 0.42. The increase in the rate of deacylation in the presence of the apolar environment and carboxylate ion of the active site of chymotrypsin indicates the operability of the charge relay system. However, since the rate acceleration is modest, and chymotrypsin uses an intramolecular carboxylate ion, it is essential to have an intramolecular carboxylate ion on the chymotrypsin model. The intramolecular carboxylate ion can be attached to the chymotrypsin model in accordance with the procedures shown in (Mallick, et al., *J. Am. Chem. Soc.*, 106, 7252–7254 (1984). The acyl-chymotrypsin model has a rate of hydrolysis of $10^5$ to $10^6$ (154,000) faster than a normal cinnamate ester and is only 18 fold slower than deacylation of real trans-cinnamoyl-chymotrypsin.

In accordance with the present invention, the binding site (cyclodextrin) and the catalytic site (o-imidazolylbezoic acid) of chymotrypsin having been established, wherein the catalytic site is placed on the secondary side of the cyclodextrin since the bound substrate would have its carbonyl function near the secondary side, the synthesis can be achieved by the following reactions:

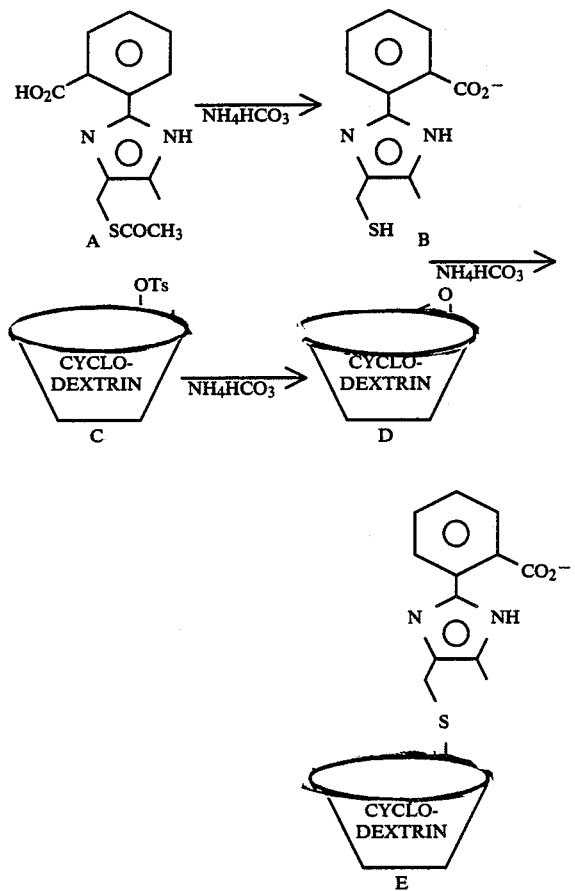

The product was purified by anion exchange chromatography, 96% purity by UV analysis.

The chymotrypsin model was examined for its catalytic activity in ester hydrolysis. Table II indicates that both the artificial and real enzymes are comparable in their catalytic activity both in rate and binding constants.

TABLE II

The Hydrolysis of Esters by Chymotrypsin (Real and Artificial)

| enzyme | substrate | $pH^c$ | $k_{cat} \times 10^{-2d}$ $(sec^{-1})$ | $K_m \times 10^{-5d}$ (M) | $k_{cat}/K_m^e$ (M $sec^{-1}$) |
|---|---|---|---|---|---|
| chymotrypsin$^a$ | p-nitrophenyl acetate | 8.0 | 1.1 | 4.0 | 275 |
| artificial chymotrypsin$^b$ | m-t-butylphenyl acetate | 10.7 | 2.8 | 13.3 | 210 |

$^a$The concentration of the stock solution was determined to be $1.0 \times 10^{-3}$ M (83% purity) by active site titration (Schonbaum, G. R., et al., J. Biol. Chem., 236, 2930–2935 (1961)).
$^b$The concentration of the stock solution was determined to be $3 \times 10^{-3}$ M (96% purity) by UV absorbance.
$^c$The pH selected was the predetermined optimum pH for both the real and artificial chymotrypsins.
$^d$The error limit in $k_{cat}$ is ± 5%; the error limit in $K_m$ is ± 10%.
$^e(k_{cat}/K_m)_{real}/(k_{cat}/K_m)_{art.} = 1.3$.

Turnover (catalysis) was proven by making a plot (FIG. 1) of product formation versus time with a concentration ratio of substrate to enzyme of 2.5. Observation of stoichiometric ratio of S/E shows no discontinuity but rather the curve continues until the two and one-half excess of product is formed, indicating that there is a turnover.

Figure 2:
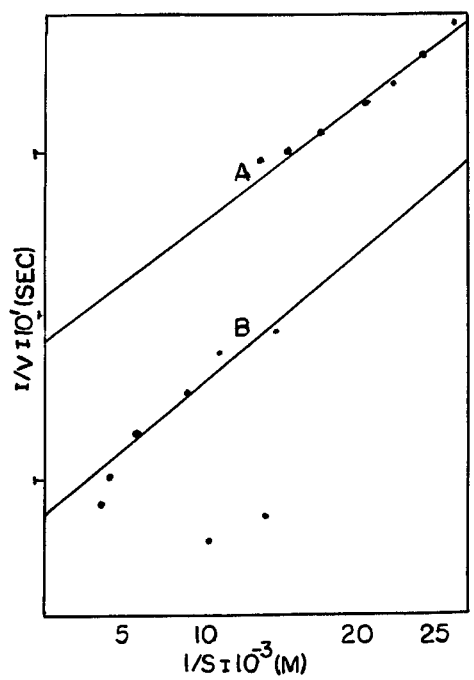
FIG. 2 graphically represents a Lineweaver-Burk plot of artificial (B) and real (A) chymotrypsin with concentrations of the substrate greater than the enzyme.

FIG. 2 shows the Lineweaver-Burk plots of artificial (B) and real (A) chymotrypsin with concentrations of the substrate greater than the enzyme (9 fold excess) again indicating there is a turnover. In FIG. 2 plot A represents the hydrolysis of p-nitrophenyl acetate by chymotrypsin and plot B represents the hydrolysis of m-t-butylphenyl acetate by the miniature organic model of chymotrypsin. $[E_A] = 1 \times 10^{-5} M$; $[E_B] = 3 \times 10^{-5} M$.

Figure 3:
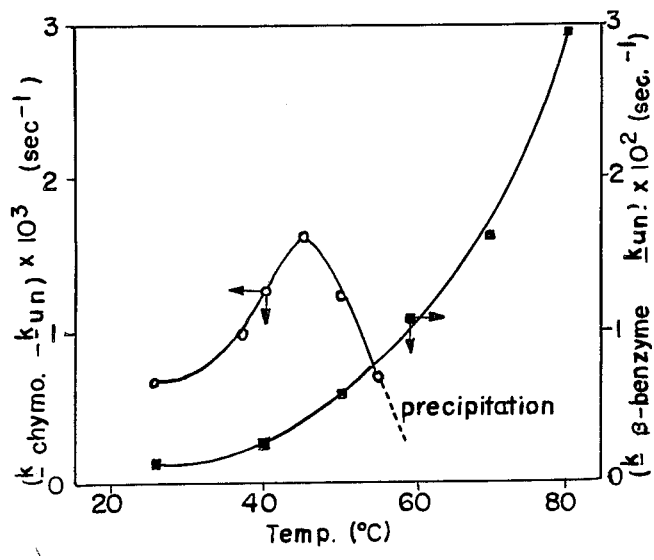
FIG. 3 graphically represents the relative stability of both real and artificial chymotrypsin at elevated temperatures.

FIG. 3 depicts the relative stability of both β-benzyme/m-t-butylphenyl acetate ( ) and α-chymotrypsin/p-nitrophenyl acetate (O) at elevated temperatures. The real enzyme has 245 amino acids whose conformation can be changed by disrupting hydrogen bonds by elevated temperature. In contrast, the artificial chymotrypsin has no amino acids. Abbreviations are explained by the equation $$k_{chymo} = k_{chymotrypsin}; k_{un} = k_{uncatalyzed}$$
$$\beta\text{-benzyme} = (D = \beta\text{-cyclodextrin in Formula 1})$$

The stability was obtained by determining the catalytic rate constant at various temperatures at pH 8.0 for chymotrypsin, using 400 nm with a Varian 200 spectrophotometer. β-benzyme activity for the artificial enzyme was determned at its optimum pH 10.7 and 288 nm.

EXAMPLE I

Synthesis of 2-[4(5)-methyl-2-imidazolyl]benzoic acid

Pyruvic aldehyde (13.5 g of 40% aqueous solution) was added dropwise to a solution of 7.5 g of o-carboxybenzaldehyde in 40 ml conc. aqueous ammonia over 2 hours. The reaction mixture was refluxed for 3 hours and extracted with ether continuously overnight. It was then acidified with 6N HCl to pH 2. It was then evaporated to dryness and crystallized from water. The product obtained in 63% yield was analyzed by proton NMR and mass spectrum to show that it was 2-[4,(5)-methyl-2-imidazolyl]benzoic acid.

EXAMPLE II

Synthesis of 2-[4(5)-methyl-4(5)-hydroxymethyl-2-imidazolyl]benzoic acid

Formaldehyde (1.2 ml of 37% aqueous solution) was added to a solution of 1.1 g 2-[4(5)-methyl-2-imidazolyl]benzoic acid in 40 ml of 1:1 aqueous ethanol and 0.647 g KOH and refluxed for 1½ hours. The reaction mixture was acidified to pH 5 with 6N HCl and evaporated to dryness. The product obtained was dissolved in dimethylfuran and filtered. The precipitate was recrystallized with water. The filtrate was evaporated and the product was crystallized from water. Both the crystallized products were combined to yield 70% of the product which on analysis by proton NMR and mass spectrum showed to be 2-[4(5)-methyl-4(5)-hydroxymethyl-2-imidazolyl]benzoic acid.

EXAMPLE III

Synthesis of 2-[4(5)-methyl-4(5)-chloromethyl-2-imidazolyl]benzoic acid

2-[4(5)-methyl-4(5)-hydroxymethyl-2-imidazolyl]-benzoic acid (1 g) was added to 10 ml of thionyl chloride at $-78°$. The reaction mixture was kept at 0° for 5 minutes. Thionyl chloride was evaporated at 0° under vacuum and 50 ml of benzene was added and the flask was stirred and benzene decanted. Dry ether, 50 ml, was added and stirred overnight and then the precipitate was filtered to obtain the desired 2-[4(5)-methyl-4(5)-chloromethyl-2-imidazolyl]benzoic acid in 95% yield. The product was analyzed by proton NMR.

EXAMPLE IV

Synthesis of 2-[4(5)-methyl-4(5)-thioacetomethyl-2-imidazolyl]benzoic acid

Potassium thioacetate (300 mg) was added to a solution of 500 mg of 2[4(5)-methyl-4(5)-chloromethyl-2-imidazolyl]benzoic acid in 50 ml of dimethylfuran and the reaction mixture was stirred at room temperature overnight. The reaction mixture was acidified with methanolic HCl to pH 5 and filtered. The filtrate was evaporated to dryness and the product was purified by flash column chromatography using silica gel. The pure product obtained in 55% yield was analyzed by NMR to be 2[4(5)-methyl-4(5)-thioacetomethyl-2-imidazolyl]-benzoic acid.

EXAMPLE V

Synthesis of β-cyclodextrin-2-tosylate

β-cyclodextrin-2-tosylate was synthesized using m-nitrophenyl tosylate and β-cyclodextrin according to the procedure reported in Tetrahedron Lett., 23, 3451 (1982). The product was analyzed by proton and $^{13}C$ NMR to show that it was β-cyclodextrin-2-tosylate.

EXAMPLE VI

Synthesis of the chymotrypsin model

Ammonium bicarbonate (20 mg) was added to a solution of 100 mg of β-cyclodextrin-2-tosylate in 5 ml water and the flask was completely rid of oxygen by freeze thaw method and kept at 60° for 3 hours under nitrogen. Ammonium bicarbonate (50 mg) was added to a solution of 100 mg of the thioacetate in 5 ml water and the flask was completely rid of oxygen and stirred at room temperature for three hours under nitrogen. After three hours the solution containing the thioacetate was transferred into the flask containing the tosylate by means of a cannula under nitrogen. The reaction mixture was stirred at 60° overnight. The reaction mixture was then evaporated to dryness under vacuum and 1 ml of water was added to the flask and stirred for 1 hour and then filtered. The filtrate was passed through an anion exchange column containing Deae Sephacel brand anion exchange resin (Sigma 1-60505). The column was eluted with double distilled water and fractions of 3 ml per hour were monitored by UV at 280 nm and collected. The fractions showing the absorbance were pooled and evaporated and analyzed by proton NMR and UV to show that it was the desired chymotrypsin model.

Having shown and described a preferred embodiment of the present invention, it should be realized that changes could be made and other examples given without departing either from the spirit or scope of this invention.

We claim:

1. A chymotrypsin model having the formula

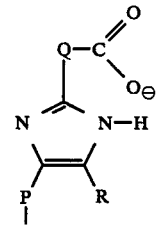

wherein D is α-, β- or γ-cyclodextrin; P is X or $(CH_2)_nX$, wherein n is 0 to 2 and X is S, NH, or O; Q is substituted phenyl with the carboxylate ion attached to the ortho position or $(CH_2)_n$, wherein n is 0 to 3; and R is hydrogen, $-CH_3$ or $-C_2H_5$.

2. The compound of claim 1 wherein the molecular weight is 1,365.

3. The compound of claim 1 wherein D is β-cyclodextrin.

4. The compound of claim 1 wherein D is γ-cyclodextrin.

5. The compound of claim 1 wherein D is α-cyclodextrin.

6. The compound of claim 3 wherein Q is substituted phenyl with the carboxylate ion attached to the ortho position.

7. The compound of claim 3 wherein P is S.

8. The compound of claim 3 wherein R is H.

9. The compound of claim 4 wherein Q is substituted phenyl with the carboxylate ion attached to the ortho position.

10. The compound of claim 4 wherein P is S.

11. The compound of claim 4 wherein R is H.

12. The compound of claim 5 wherein Q is substituted phenyl with the carboxylate ion attached to the ortho position.

13. The compound of claim 5 wherein P is S.

14. The compound of claim 5 wherein R is H.

15. The compound $3^A$-S-[[2-(2-carboxyphenyl)-5-methyl-1H-imidazol-4-yl]-methyl]-$3^A$-thio-$\beta$-cyclodextrin.

16. The compound $3^A$-s-[[2-(2-carboxyphenyl)-5-methyl-1H-imidazol-4-yl]-methyl]-$3^A$-thio-$\gamma$-cyclodextrin.

17. The compound $3^A$-S-[[2-(2-carboxyphenyl)-5-methyl-1H-imidazol-4-yl]-methyl]$3^A$-thio-$\alpha$-cyclodextrin.

* * * * *

UNITED STATES PATENT AND TRADEMARK OFFICE
CERTIFICATE OF CORRECTION

PATENT NO. : 4,777,250

DATED : October 11, 1988

INVENTOR(S) : Myron L. Bender and Valerian T. D'Souza

It is certified that error appears in the above-identified patent and that said Letters Patent is hereby corrected as shown below:

In Column 6, line 37, delete "( )", insert --(■)--.

Signed and Sealed this

Twenty-eighth Day of March, 1989

Attest:

DONALD J. QUIGG

Attesting Officer

Commissioner of Patents and Trademarks